United States Patent
Cao et al.

(10) Patent No.: US 10,412,941 B2
(45) Date of Patent: Sep. 17, 2019

(54) ARTIFICIAL FEEDING METHOD AT LOW ALTITUDE FOR HOST INSECT GHOST MOTH OF OPHIOCORDYCEPS SINENSIS

(71) Applicant: GUANGDONG ENTOMOLOGICAL INSTITUTE, Guangzhou, Guangdong (CN)

(72) Inventors: Li Cao, Guangzhou (CN); Richou Han, Guangzhou (CN)

(73) Assignee: GUANGDONG INSTITUTE OF APPLIED BIOLOGICAL RESOURCES, Guanzhou, Guangdong (CN)

( * ) Notice: Subject to any disclaimer, the term of this patent is extended or adjusted under 35 U.S.C. 154(b) by 170 days.

(21) Appl. No.: 15/117,330

(22) PCT Filed: Dec. 2, 2014

(86) PCT No.: PCT/CN2014/092751
§ 371 (c)(1),
(2) Date: Aug. 8, 2016

(87) PCT Pub. No.: WO2016/026237
PCT Pub. Date: Feb. 25, 2016

(65) Prior Publication Data
US 2016/0345554 A1    Dec. 1, 2016

(30) Foreign Application Priority Data
Aug. 20, 2014   (CN) .......................... 2014 1 0413333

(51) Int. Cl.
A01K 67/033   (2006.01)
(52) U.S. Cl.
CPC ................................ *A01K 67/033* (2013.01)

(58) Field of Classification Search
CPC .. A01K 67/033; A01K 67/0332; A01K 97/04; A01K 45/007; A01K 67/00; A01N 63/00
(Continued)

(56) References Cited

FOREIGN PATENT DOCUMENTS

| CN | 101940192 A | 1/2011 |
|---|---|---|
| CN | 102487905 A | 6/2012 |

(Continued)

OTHER PUBLICATIONS

International Search Report dated May 25, 2015, issued in counterpart International Application No. PCT/CN2014/092751 (2 pages).

*Primary Examiner* — Tien Q Dinh
*Assistant Examiner* — Ebony E Evans
(74) *Attorney, Agent, or Firm* — Westerman, Hattori, Daniels & Adrian, LLP

(57) ABSTRACT

An artificial feeding method at low altitude for a host insect ghost moth of Ophiocordyceps sinensis including selecting an appropriate disinfectant for performing surface disinfection on ghost moth eggs, and then placing the disinfected eggs in sterile humus; feeding ghost moth larvae with carrots, disinfecting and detecting the fed carrots, and culturing the larvae till male and female pupae are obtained; identifying male and female pupae of the ghost moths, placing them at different culture temperatures, wherein the culture temperature for the male pupae is 2-6° C. lower than that of the female pupae, resulting synchronously emerged male and female adults; placing the emerged male and female adults in an adult cage with simulated plants for mating and staying of the adults, maintaining a humidity over 80%, and employing 50-100 Lux shimmer for facilitating activity and mating of the adults.

2 Claims, 2 Drawing Sheets

(58) Field of Classification Search
USPC .......................................... 119/6.5, 6.6, 6.7
See application file for complete search history.

(56) References Cited

FOREIGN PATENT DOCUMENTS

| | | |
|---|---|---|
| CN | 102696555 A | 10/2012 |
| CN | 102813081 A | 12/2012 |
| CN | 102835358 A | 12/2012 |
| CN | 102960183 A | 3/2013 |
| CN | 103081869 A | 5/2013 |
| CN | 103168753 A | 6/2013 |
| CN | 103548780 A | 2/2014 |

…
ARTIFICIAL FEEDING METHOD AT LOW ALTITUDE FOR HOST INSECT GHOST MOTH OF OPHIOCORDYCEPS SINENSIS

FIELD OF THE INVENTION

The present invention belongs to the field of insect breeding, particularly relates to an artificial feeding method at low altitude for a host insect ghost moth of Ophiocordyceps sinensis.

BACKGROUND OF THE INVENTION

Ophiocordyceps sinensis (synonym: Cordyceps sinensis) is the most unique biological resource in China, belongs to Ascomycota, Sordariomycetes, Hypocreales, Ophiocordycipitaceae, Ophiocordyceps, and mainly originates in Tibet, Qinghai, Yunnan, Sichuan, Gansu and other snow-capped and cold highland areas with an altitude over 3,000 meters in China. Ophiocordyceps sinesis fungus infects host insect, i.e., ghost moth larva and inactivates it, and the fungus-infected inactivated insect grows under a suitable condition to form an insect (inactivated insect) and grass (fungal fruiting body) composite morphological structure which is the authentic medicinal Ophiocordyceps sinensis.

Medicinal and edible Ophiocordyceps sinensis is excellent in a plurality of functions, such as tonifying liver and kidney, benefiting vital energy, regulating various consumptive diseases. In modern medicine, Ophiocordyceps sinensis is regarded as a natural immune regulator, a "natural large combination therapy" for human health care. Ophiocordyceps sinensis may produce a variety of physiologically active substances with anti-bacterial, anti-viral, anti-tumor, anti-radiation and immune-regulating functions, and has a wide application in medicine, food and modern biotechnology, etc., especially plays an important role in traditional tonic market in China, always wins trust and favor from nationals, and realizes hot sell in Japan, Korea, Southeast Asia, the United States and other international markets.

Depletion of resources, strong demands and protection policies lead to its soaring market price. Wild Ophiocordyceps sinensis has been listed as species under national secondary protection. In order to protect Qinghai-Tibet Plateau ecology and Ophiocordyceps sinensis resources so that Ophiocordyceps sinensis better serves human health, the only option is artificial cultivation.

Artificial propagation of a host insect ghost moth (Lepidoptera, Hepialidae) of Ophiocordyceps sinensis fungi, is an important part of artificial cultivation of Cordyceps sinensis. It is reported that over 60 species of ghost moth insects are distributed in Yunnan, Tibet, Sichuan, Qinghai and Gansu. Ghost moths are holometabolous insects, the life cycle of which includes egg, larva, pupa and adult stages. The most suitable soils for growth are alpine meadow and scrubland soils. Life cycles of ghost moth species vary in different areas, but on the whole the life cycles are regular. Pupae emerge into adults in June to August every year. After mating of male and female insects, the female insects shall immediately scatter the eggs in the nearby grass or shrub vegetation. Generally each female ghost moth lays 200-800 eggs. Ghost moth larva have a tunnel-type life in natural soil and are omnivorous with plant tender roots as main food. Larvae have to go through a long period of growth and development, generally 7-9 instars (900-1300 days) for pupation, and there is a significant metagenesis phenomenon in the period. Ghost moth larvae are dormant in the soils during soil-freezing period from October every year to April of next year. Ghost moth larvae start to form pupae in late May each year, and then emerge into adults after pupa stage of 1-3 months. In the natural environment the whole generation cycle of the ghost moth insects is accomplished by comprehensive controls on multiple ecological factors including species, geographic distribution, food, vegetation, soil structure, temperature, humidity and natural enemies and the like.

In the artificial feeding process of ghost moth insects, feed quality, pathogen pollution, low survival rate of larvae, inconsistent developmental stages of male and female pupae, low mating opportunities of adults are critical constraints.

SUMMARY OF THE INVENTION

The objective of the present invention is to provide an artificial feeding method at low altitude for a host insect ghost moth of Ophiocordyceps sinensis.

The artificial feeding method at low altitude for a host insect ghost moth of Ophiocordyceps sinensis of the present invention comprising the following steps:

a. Egg stage management: performing surface disinfection on eggs laid by ghost moth adults to kill bacteria and control fungi, then placing the disinfected eggs in sterile humus.

The most critical step in egg stage management is performing surface disinfection on eggs laid by adults. An appropriate disinfectant can remove harmful microorganisms on surfaces of eggs, and improve survival rate of larvae. The preferable method is washing eggs with sterile water for several times and then disinfecting with a disinfectant for 3-6 minutes, filtering out and then washing with sterile water for several times again. The disinfectant is prepared by adding 150 ml 4 mol NaOH solution, 50 ml sodium hypochlorite (the content of active chlorine ≥7.5%) to 1000 ml sterile water. This disinfection method can kill the bacteria and also control fungi. The medium for insect cultivation used in the present invention is commercially available humus. Humus contains no heavy metal pollutants, not only has good moisturizing effect, but also serves as feeding substance for hungry larvae. Humus generally contains 40% of water, and the humus used in the present invention preferably contains 35-45% of water. The humus added to culture vessels (plastic bottles, glass bottles, etc.) can be used for feeding ghost moth insects after high pressure disinfection (121° C., 30-60 minutes). Eggs disinfected with the disinfectant are placed in the above humus. Different amounts of humus and insect eggs are added in accordance with the volume of the culture vessel, generally one egg added in per gram of humus.

b. Larva stage management: feeding ghost moth larvae with carrots, disinfecting and detecting the fed carrots to ensure that the fed carrots are harmless to ghost moth larvae, thus obtaining male and female pupae.

Carrots harmful to larvae are mainly due to pesticide residues in the production process as well as possible pathogenic microorganisms carried in the production and transportation processes, such as *Beauveria bassiana, Metarhizium anisopliae, Penicillium expansum, Isaria farinose* and *Pseudomonas* sp., etc. The preferred method, whether for detection of pesticide residues or pathogenic microorganisms, is washing the carrots with sterile water and aqueous ethanol with volume fraction of 75%, dicing the washed carrots and then sampling every piece (or every batch) to feed ghost moth larvae at least two days to detect whether the carrots have a lethal effect on larvae, and preserving the remaining carrots at low temperature for later use, if samples do not cause harm to larvae, the carrots preserved at low temperature can be used for feeding larvae. Performing surface disinfection on carrots with 75% ethanol reduces the number of pathogens, especially bacteria to some extent. Use of a feeding detection method can avoid harm of harmful carrots to ghost moth larvae, thus enhancing the survival rate of larvae.

c. Pupa stage management: identifying male and female pupae of ghost moths, placing the male and female pupae at different culture temperatures, that is, the culture temperature of male pupae is 2-6° C. lower than that of female pupae, such that development of the male pupae becomes slow and is synchronous with that of the female pupae.

Ensuring synchronous emergence of the male and female pupae is critical to the pupa stage management. The emergence over the same period is a precondition for successful mating of the male and female insects. Male and female pupae entering the pupa stage at the same time have inconsistent emergence time, wherein the emergence time of the male pupae is earlier than that of female ones in general. The method provided in the present invention is to place the male and female pupae at different culture temperatures based on correct identification of male and female pupae, that is, the culture temperature of male pupae is generally lower than that of female pupae so that the development of the male pupae becomes slow to realize synchronous development with the female pupae. Temperature differences between male and female pupae are various for different ghost moth species, generally 2-6° C.

d. Adult stage management: placing the emerged male and female adults in an adult cage in which simulated plants are placed for mating and staying of the adults, maintaining a humidity over 80%, employing 50-100 Lux shimmer for facilitating activity and mating of adults, and collecting eggs after adults lay eggs.

The key for adult stage management is to facilitate mating of male and female adults and successful laying of the female insects. Measures took in the present invention are using plant-like plastic products, assisted with shimmer (50-100 Lux) to facilitate activity and mating of adults.

The artificial feeding method at low altitude for a host insect ghost moth of Ophiocordyceps sinensis of the present invention can effectively solve the problems of the prior art, including contamination, low survival rate of larvae, inconsistent development of male and female pupae, low mating opportunity of adults and the like in the artificial feeding process at low altitude for ghost moths, and provides an effective technology for large-scale production of Ophiocordyceps sinensis.

BRIEF DESCRIPTION OF THE DRAWINGS

FIG. 1-B is a photograph showing the morphological features of the last segment of a female pupa.

FIG. 1-C is a photograph comparing the sizes of male and female pupae.

DETAILED DESCRIPTION OF THE EMBODIMENTS

Figure 1:
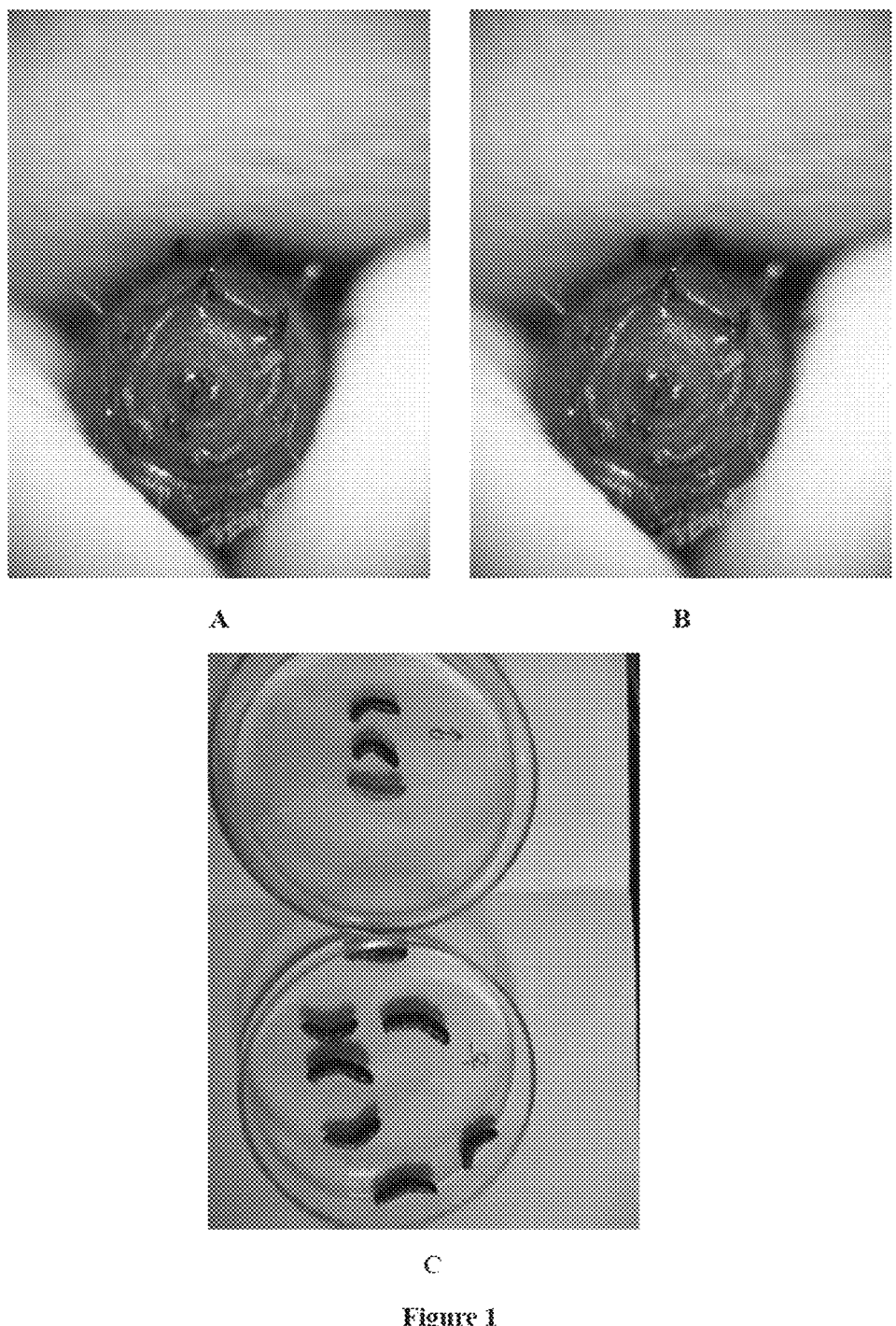
FIG. 1-A is a photograph showing the morphological features of the last segment of a male pupa.

The following examples further illustrate the present invention, rather than limiting the present invention.

EXAMPLE 1

Ghost moths used in the present invention are from Yunnan Thitarodes jianchuanensis, Sichuan Thitarodes gonggansis, and Tibet and Qinghai Thitarodes armoricanus.

(1) Egg Stage Management 10 g of commercially available humus containing 35-45% of water was added to a 50 ml glass bottle (matrix for sowing, white peat 705, Tref company), high pressure disinfection (121° C., 60 minutes) was performed, and the humus was placed at 9-16° C. for cooling and later use.

At a low temperature (9-16° C.), eggs produced indoor by ghost moth adults were collected in a sterile plastic centrifuge tube (50 ml), each tube containing about 20,000 eggs; the eggs were poured into a 100-mesh sterile gauze, and the eggs were gently washed with sterile water at least three times; the eggs-carrying gauze was placed in a 200 ml disinfectant to perform disinfection for 3-6 minutes (depending on different species of ghost moths), and the eggs were washed in sterile water respectively at least 3 times after the gauze was taken out from the disinfectant; disinfected eggs were added to humus-carrying culture bottles with 10 eggs per bottle, and different amounts of humus and eggs were added based on volume of the culture vessels, generally one egg in per gram (containing 35-45% of water) of humus; and hatching of eggs was observed at 9-16° C. After 35-40 days, the eggs were hatched, and the larvae made activities on the surface of and inside the humus. The disinfectant was an even mixture obtained by adding 15 ml 4 M NaOH solution and 5 ml sodium hypochlorite solution (the content of active chlorine ≥7.5%) to 100 ml sterile water. Samples (about 30 eggs) were added to an LB (tryptone 10 g, yeast powder 5 g, NaCl 5 g, agar 18 g, with pH=7.2, adding water to 1000 mL) and PPDA (glucose 20 g, potato 200 g, peptone 10 g, $KH_2PO_4$ 3 g, $MgSO_4 \cdot 7H_2O$ 1.5 g, $VB_1$ 0.02 g, agar powder 15 g, $H_2O$ 100 mL, with natural pH) medium, disinfection effect was inspected after culturing at 15° C. and 25° C. respectively for 25 days; meanwhile the eggs were placed in a 9 cm sterile culture dish (adding filter paper of sterile water for moisturizing according to different eggs) for hatching at 16° C. and hatchability was calculated after 30-45 days. The results proved that the disinfectant used in the present invention could effectively kill microorganisms on egg surface, and no microbial growth was found on LB and PPDA media after culturing for 45 days at 15° C. and 25° C.; egg surface disinfection did not affect egg hatchability, and the hatchability did not differ significantly for disinfected and non-disinfected eggs.

(2) Larva Stage Management

After ghost moths entered the larva stage, fresh carrots were added on humus as the feed for larva. Generally the feed was added once every four weeks. According to larvae instar and development of the larva, about 1-10 g fresh carrots were added to each culture bottle every time.

In the feeding process, larvae were often infected by pathogens or chemical pesticide residues carried by carrots. Thus, carrots for use should had no pesticide residues, and also carried no pathogens harmful to the larvae.

To ensure quality of carrots, in addition to washing with sterile water and then disinfecting the carrots to he used with ethanol of 75% volume fraction, the most important method was to dice the carrots washed with sterile water and then perform disinfection with ethanol of 75% volume fraction, and sample every piece (or every batch) to feed a small number of ghost moth larvae at least two days for detecting whether the carrots have a lethal effect on larvae. The remaining carrots were placed in a 4° C. refrigerator for later use. If the tested carrots did not cause harm to the larvae, those carrots in the 4° C. refrigerator could be used. Compared with using carrots without detection, this step could effectively detect the quality of used carrots, greatly reduce larval mortality as a result of pesticide residues and harmful microorganisms, and increase larval survival rate by 30%.

(3) Pupa Stage Management

Figure 2:
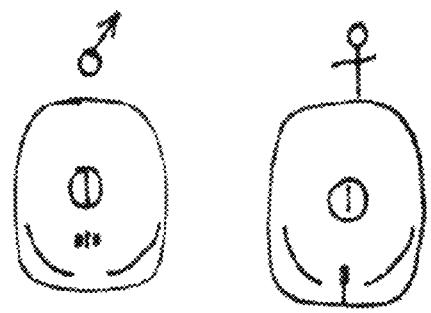
FIG. 2 is a hand-drawn diagram thereof.

At 9-13° C., larvae entered the pupa stage after 7-9 instars, 136-263 days for Yunnan Hepialus, 256-545 days for Sichuan Hepialus larvae, and 214-660 days for Qinghai Hepialus. Male pupae were generally small, while female pupae were different in size. The distinguishing feature between male and female pupae was the ventral crack and protuberance of the very last segments of pupae. It was found there were two dark arcs on the two lateral sides of the ventral center line by observing a tail last segment with naked eyes. A male pupa had two distinct black spots between the anus and the arcs, while a female pupa obviously had a vertical crack line in the middle of the arcs, as shown in FIGS. 1-A, 1-B and 1-C, wherein FIG. 1-A showed morphological features of the last segment of a male pupa. FIG. 1-B showed morphological features of the last segment of a female pupa. FIG. 1-C compared the sizes of male and female pupae, and a hand-drawn diagram thereof was as shown in FIG. 2.

Since male pupae generally emerged earlier than female pupae, to control synchronous emergence of male and female pupae and ensure successful mating of the male and female pupae, newly pupated male pupae were placed at 10° C., while the female pupae were placed at 13° C., such that male and female pupae basically emerged simultaneously. At 9-13° C., the pupa stage was generally 34-42 days for Yunnan Hepialus. 35-45 days for Sichuan Hepialus, 38-50 days for Qinghai Hepialus.

(4) Adult Stage Management

Preparation of an adult cage: a commercially available baby mosquito net (volume=104 cm×50 cm×50 cm) was washed and dried, and sterilized cotton cloth was placed at the bottom of the cage for easy collection of laid eggs.

At 9-13° C., when pupae emerged into adults, first male and female adults were identified, and then they were added to the cage following a male to female ratio at 1:1, 100-200 adults were added to each cage. Plastic flowers undergoing ultraviolet overnight irradiation were added to the adult cage for mating and staying of adults. If necessary, a humidifier was required to maintain a humidity over 80%; 15 W lamplight provided scattered light (with light intensity of 50-100 Lux), being beneficial for flying, wing-spreading and mating of adults. Maybe due to an increase of adult mating opportunity, the opportunity for female egg fertilization was also increased. Therefore, the hatchability of eggs was increased by 30-50% over the previous.

After mating of adults, the female adults began to lay eggs. Be noted to collect eggs in a timely manner (first ivory, turning to black after 3-5 hours). The best time to collect eggs was 8-10 hours after laying. The eggs were put in a culture dish (diameter=9 cm) containing sterile filter paper with appropriate humidity. Female ghost moth insects of different species produced varying amounts of eggs, generally 200-800 eggs per female adult.

The invention claimed is:

1. An artificial feeding method at low altitude for a host insect ghost moth of Ophiocordyceps sinensis, comprising the following steps:
    (a). managing an egg stage by performing surface disinfection on a first egg laid by ghost moth adults to kill bacteria and control fungi to form a disinfected egg and, then placing the disinfected egg in sterile humus;
    (b). managing a larva stage by feeding ghost moth larvae with carrots, wherein the step (b) comprises washing the carrots with sterile water and aqueous ethanol with volume fraction of 75%, dicing the carrots and then sampling a portion of the carrots by feeding the ghost moth larvae for at least two days to detect whether the carrots have a lethal effect on larvae, and preserving a remaining portion of the carrots at low temperature for later use, wherein if the portion of the carrots sampled does not cause harm to larvae, the remaining portion of the carrots preserved at low temperature can be used for feeding larvae to obtain male pupae and female pupae;
    (c). managing a pupa stage by identifying the male pupae and the female pupae of ghost moths, placing the male pupae and the female pupae at different culture temperatures, wherein the culture temperature of the male pupae is 2-6° C. lower than that of the female pupae, such that development of the male pupae becomes slow and is synchronous with that of the female pupae; and
    (d). managing an adult stage by placing male adults and female adults that have emerged from the pupa stage (c) in an adult cage in which simulated plants are placed for mating and staying of the male adults and the female adults, maintaining a humidity over 80%, employing 50-100 Lux shimmer for facilitating activity and mating of the male adults and the female adults, and collecting a second egg after the female adults lay the second egg.

2. The artificial feeding method at low altitude for a host insect ghost moth of Ophiocordyceps sinensis according to claim 1, wherein surface disinfection in step (a) comprises washing the first egg with sterile water for several times and then disinfecting with a disinfectant for 3-6 minutes, filtering out and then washing with sterile water for several times again, the disinfectant is prepared by adding 150 ml 4 mol NaOH solution, 50 ml sodium hypochlorite (the content of active chlorine ≥7.5%) to per 1000 ml sterile water, and the humus contains 35-45% of water.

* * * * *